United States Patent
Sasaki et al.

(10) Patent No.: US 7,475,697 B2
(45) Date of Patent: Jan. 13, 2009

(54) CLEANING DEVICE FOR MEDICAL INSTRUMENTS

(75) Inventors: Katsumi Sasaki, Tokyo (JP); Shinya Masuda, Tokyo (JP); Eiji Murakami, Tokyo (JP); Ryoji Masubuchi, Tokyo (JP)

(73) Assignee: Olympus Corporation (JP)

( * ) Notice: Subject to any disclaimer, the term of this patent is extended or adjusted under 35 U.S.C. 154(b) by 314 days.

(21) Appl. No.: 11/469,339

(22) Filed: Aug. 31, 2006

(65) Prior Publication Data

US 2006/0289043 A1 Dec. 28, 2006

Related U.S. Application Data

(62) Division of application No. 10/659,175, filed on Sep. 10, 2003, now abandoned.

(30) Foreign Application Priority Data

Sep. 13, 2002 (JP) ............................. 2002-268731

(51) Int. Cl.
*B08B 3/02* (2006.01)

(52) U.S. Cl. .................. 134/166 C; 134/167 C; 134/198

(58) Field of Classification Search ........... 134/166 C, 134/169 C, 167 C, 198

See application file for complete search history.

(56) References Cited

U.S. PATENT DOCUMENTS

| 582,148 | A | * | 5/1897 | Rollins ..................... 138/90 |
| 4,537,209 | A | * | 8/1985 | Sasa ....................... 134/166 C |
| 4,667,655 | A | * | 5/1987 | Ogiu et al. ................. 600/132 |
| 4,872,837 | A | * | 10/1989 | Issalene et al. ............... 433/29 |
| 5,448,795 | A | * | 9/1995 | Boughal ..................... 15/406 |
| 5,474,130 | A | * | 12/1995 | Davis ....................... 166/312 |
| 5,840,251 | A | * | 11/1998 | Iwaki ........................ 422/36 |
| 6,485,412 | B1 | * | 11/2002 | Byrne ...................... 600/158 |
| 6,485,684 | B1 | * | 11/2002 | Mapson et al. ............... 422/28 |

FOREIGN PATENT DOCUMENTS

| DE | 42 20 701 | * | 2/1993 |
| DE | 297 04 354 | * | 6/1997 |
| JP | 2000-147390 | | 5/2000 |

* cited by examiner

*Primary Examiner*—Frankie L Stinson
(74) *Attorney, Agent, or Firm*—Ostrolenk, Faber, Gerb & Soffen, LLP (57) ABSTRACT

There is a disclosed a cleaning for a medical instrument, including a nozzle main body detachably to a surgical ultrasonic treatment instrument including a channel, and the nozzle main body includes a water supply port opened in a position connected to the channel, when mounted in the surgical ultrasonic treatment instrument.

6 Claims, 9 Drawing Sheets

CLEANING DEVICE FOR MEDICAL INSTRUMENTS

CROSS-REFERENCE TO RELATED APPLICATIONS

This application is a divisional of U.S. applicaton Ser. No. 10/659,175 filed Sep. 10, 2003, by Katsumi SASAKI, et. al., entitled CLEANING DEVICE FOR MEDICAL INSTRUMENT, and claims the benefit of priority from the prior Japanese Patent Application No. 2002-268731, filed Sep. 13, 2002, the entire contents of which are incorporated herein by reference.

BACKGROUND OF THE INVENTION

1. Field of the Invention

The present invention relates to a device for cleaning medical instruments including channels.

2. Description of the Related Art

In Jpn. Pat. Appln. KOKAI Publication No. 2000-296135, an ultrasonic treatment instrument has been proposed as a surgical treatment instrument. In general, the ultrasonic treatment instrument includes a handle unit including an insertion portion, a probe unit attached to the handle unit, and a vibrator unit for driving a probe, and these units are assembled in a disassemblable manner. A jaw which is an open/close member for grasping the ultrasonic treatment instrument is attached to a distal-end of the insertion portion of the handle unit. This jaw is connected to an operation rod inserted in a channel formed in the insertion portion of the handle unit, and is rotated, when the operation rod is moved forwards/backwards by a handle of the handle unit. Another channel for inserting the probe of the probe unit is disposed in the insertion portion of the handle unit. When the probe unit is attached to the handle unit, the probe is inserted in the channel, so that the distal-end portion of the probe is disposed opposite to the jaw.

Since this type of ultrasonic treatment instrument is a medical instrument, the instrument needs to be cleaned every use. To clean the ultrasonic treatment instrument, simple cleaning methods such as brush cleaning and shower cleaning in running water have heretofore been carried out.

In this conventional cleaning method, however, a lot of trouble and much time are required for cleaning the channel formed in the handle unit, and efficiency of a cleaning operation of an endoscope has been bad.

BRIEF SUMMARY OF THE INVENTION

An object of the present invention is to provide a cleaning device for a medical instrument, which can efficiently clean the inside of a channel disposed in the medical instrument.

According to an aspect of the present invention, there is provided a cleaning device which cleans at least one channel of a medical instrument with cleaning water, comprising:

a tubular member including a proximate-end portion and a distal-end portion which able to be inserted in an inlet of the channel of the medical instrument;

a water supply port which is disposed in the distal-end portion and which leads to the channel to supply the cleaning water to the channel, when the distal-end portion is inserted in the inlet;

a seal member which is disposed on an outer periphery of the distal-end portion and which is positioned on a proximate-end side from the water supply port to seal a gap between an outer peripheral portion of the distal-end portion and an inner surface of the channel and to constitute an engaging portion which attaches the distal-end portion inserted in the inlet to the medical instrument, when the distal-end portion is inserted in the inlet; and a port which is disposed in the proximate-end portion of the tubular member and which is connected to a water supply source of the cleaning water.

According to another aspect of the present invention, there is provided a cleaning device using cleaning water to clean both channels of a medical instrument including a first channel and second channel and a portion via which both the channels are connected to each other, comprising:

a tubular member including a proximate-end portion and a distal-end portion which able to be inserted in an inlet of the first channel of the medical instrument;

a first water supply port which is disposed in the distal-end portion and which leads to the first channel to supply the cleaning water to the first channel, when the distal-end portion is inserted in the inlet;

a first seal member which is disposed on an outer peripheral surface of the distal-end portion and which is positioned and disposed on a proximate-end side from the water supply port to seal a gap between an outer peripheral portion of the distal-end portion and an inner surface of the first channel and to constitute a first engaging portion which attaches the distal-end portion inserted in the inlet to the medical instrument, when the distal-end portion is inserted in the inlet;

a second water supply port which is disposed in the tubular member and which is positioned and disposed in a proximate-end side portion partitioned from the first water supply port by the first seal member when the distal-end portion is inserted in the inlet and which leads to the second channel to supply the cleaning water to the second channel;

a second engaging portion which is disposed in the tubular member and which is positioned and disposed on the proximate-end side from the second water supply port and which is constituted by an outer peripheral portion sealing from a seal member of the medical instrument, when the distal-end portion is inserted in the inlet;

a first port which is disposed in the proximate-end portion of the tubular member and which is connected to the first water supply port and which is to be connected to a water supply source of the cleaning water; and a second port which is disposed in the proximate-end portion of the tubular member and which is connected to the second water supply port and which is to be connected to the water supply source of the cleaning water.

According to a further aspect of the present invention, there is provided a cleaning device using cleaning water to clean channels of a medical instrument which includes a first channel which passes a treatment probe to transmit a treatment energy, a grasp member for grasping a living tissue with a distal-end portion of the treatment probe, a rod for operating the grasp member, and a second channel for passing the rod and to which a generation unit for generating the treatment energy is detachably attached, the device comprising:

an elongated member including a proximate-end portion and a distal-end portion which can be inserted in an inlet of the first channel;

an attachment member which is disposed in the proximate-end portion and which able to be attached to the medical instrument;

a first water supply port which is disposed in the distal-end portion and which supplies the cleaning water to the first channel;

a first engaging portion which includes a member disposed on an outer peripheral surface of the distal-end portion to seal a gap between the outer peripheral surface and an inner surface of the inlet and which is constituted of the member to attach the distal-end portion inserted in the inlet to the inner surface of the inlet;

a second engaging portion which is positioned and disposed on the proximate-end side from a portion for connecting the first channel to the second channel in the elongated member and which includes a large-diameter portion formed to be thicker than the distal-end portion and which engages with the medical instrument by the large-diameter portion;

a second water supply port which is positioned between the first engaging portion and the second engaging portion to open in an outer peripheral wall of the elongated member and which leads to the second channel and which supplies water to the second channel;

a first supply nozzle which is disposed in the elongated member and which is connected to the first water supply port and which is to be connected to a water supply of the cleaning water to supply the water to the first water supply port; and a second supply nozzle which is disposed in the elongated member and which is connected to the second water supply port and which is to be connected to the water supply of the cleaning water to supply the water to the second water supply port.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

With reference to FIGS. 1 to 7B, for example, a cleaning device for a surgical treatment instrument according to a first embodiment of the present invention will be described as a medical device.

Figure 1:
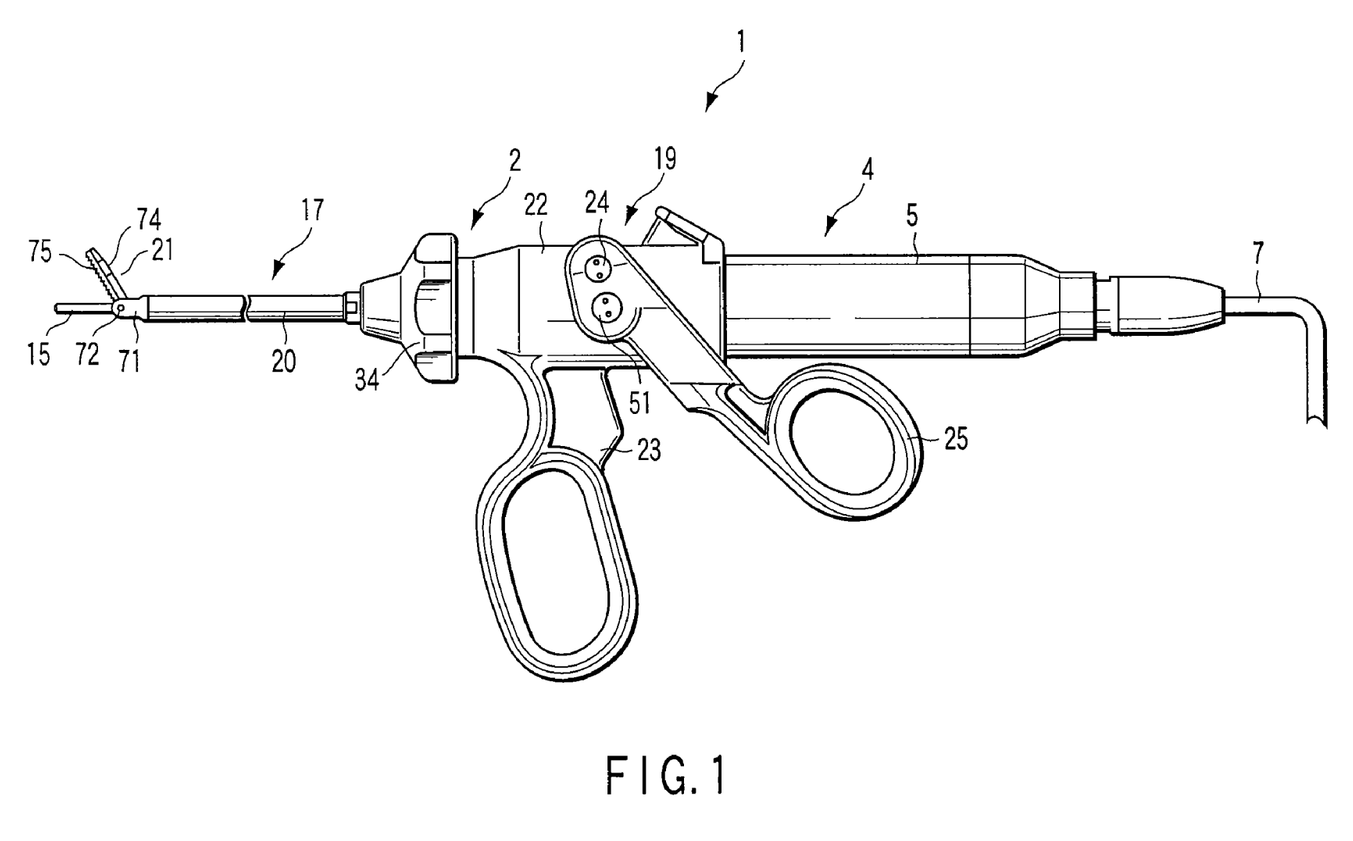
FIG. 1 is a side view of an assembled state of an ultrasonic treatment instrument according to a first embodiment of the present invention.

The surgical treatment instrument which is a cleaning object in the present embodiment is an ultrasonic treatment instrument 1. The ultrasonic treatment instrument 1 includes a handle unit 2 shown in FIG. 2, a probe unit 3 shown in FIG. 3A, and a vibrator unit 4 shown in FIG. 3B. When the ultrasonic treatment instrument 1 is used, the respective units 2, 3, 4 are assembled as shown in FIG. 1.

Figure 3A:
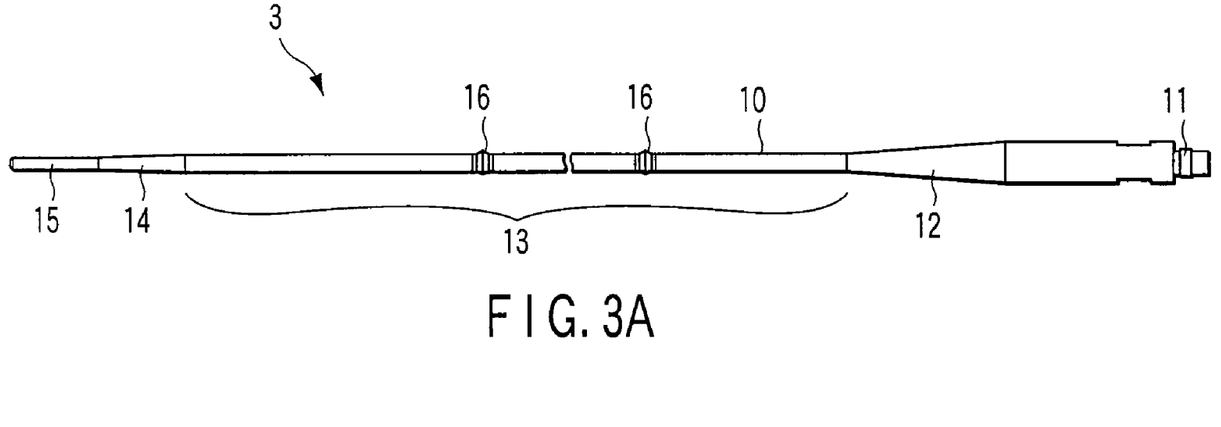
FIG. 3A is a side view of a probe unit of the ultrasonic treatment instrument.
Figure 3B:
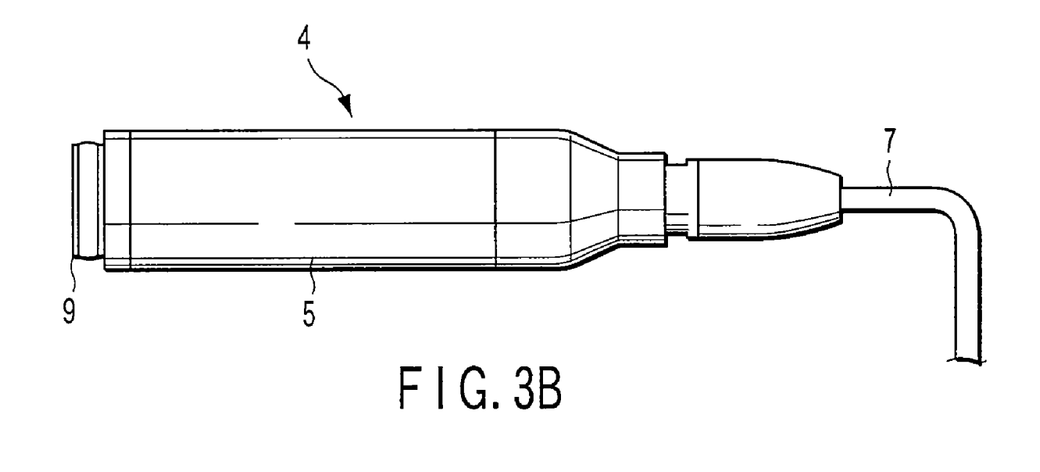
FIG. 3B is a side view of a vibrator unit.

As shown in FIG. 3B, the vibrator unit 4 includes a cylindrical exterior cover 5, and an ultrasonic vibrator and horn (not shown) are disposed in the exterior cover 5. A hand piece cord 7 to be electrically connected to a power supply source (not shown) is connected to a proximate-end of the vibrator unit 4. A power for driving is supplied to the ultrasonic vibrator from the power supply source via the hand piece cord 7 to drive the ultrasonic vibrator. A connection portion 9 to be connected to the handle unit 2 is formed in a front peripheral edge of the vibrator unit 4.

As shown in FIG. 3A, the probe unit 3 includes a rod-shaped vibration transmission member 10, and ultrasonic vibration generated in the ultrasonic vibrator of the vibrator unit 4 is transmitted to a distal-end treatment portion by this rod-shaped vibration transmission member 10. A male screw 11 to be screwed in a female screw formed in the distal-end of the horn is formed in a proximate-end position of the vibration transmission member 10. The vibration transmission member 10 includes: a conical proximate-end horn 12 for enlarging an amplitude of the ultrasonic vibration amplified by the horn on the side of the vibrator unit 4 further into a second stage; a middle portion 13 positioned on the side of a distal-end of the proximate-end horn 12; a conical distal-end horn 14, positioned on the side of the distal-end of the middle portion 13, for enlarging the amplitude of the ultrasonic vibration amplified by the proximate-end horn 12 into a final stage; and a cylindrical distal-end 15 positioned on the side of the distal-end of the distal-end horn 14. The ultrasonic vibration generated in the ultrasonic vibrator is gradually amplified by the horn of the vibrator unit 4, the proximate-end horn 12 in the vibration transmission member 10, and the distal-end horn 14, and is transmitted to the distal-end 15 of the vibration transmission member 10. In the middle portion 13 of the vibration transmission member 10, a plurality of flange-shaped support members 16 are positioned in second and subsequent nodes on the side of the distal-end of the transmitted ultrasonic vibration.

Figure 2:
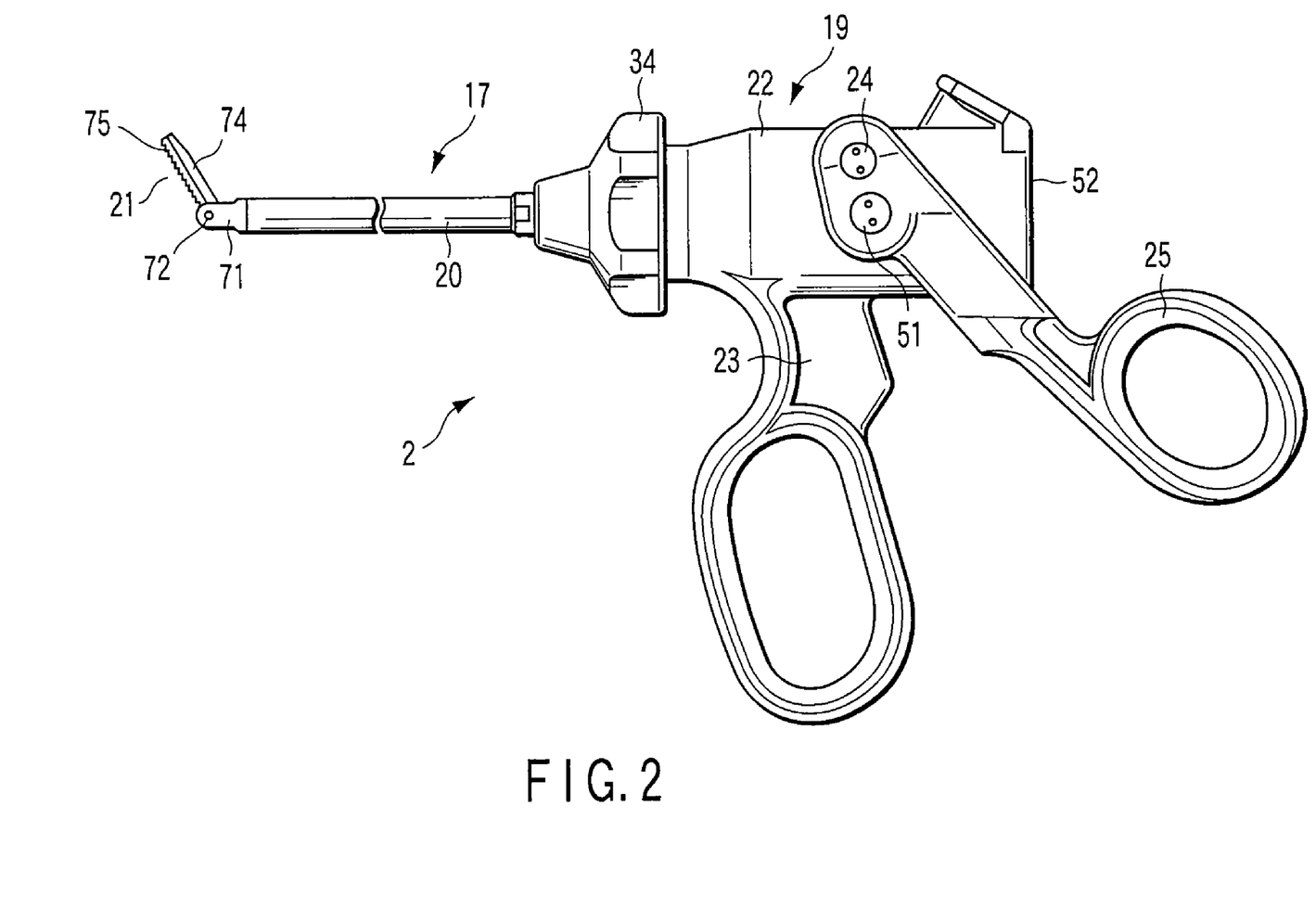
FIG. 2 is a side view of a handle unit of the ultrasonic treatment instrument.

As shown in FIG. 2, the handle unit 2 includes an operation portion 19, an insertion sheath portion 17 including a longitudinal overcoat tube 20 rotatably attached to the operation portion 19, and a distal-end function portion (treatment portion) 21 disposed in the distal-end of the insertion sheath portion 17. The operation portion 19 of the handle unit 2 includes an operation portion main body 22, a fixed handle 23 formed integrally with the operation portion main body 22, and a movable handle 25 rotatably attached to the operation portion main body 22 via a handle support shaft 24.

Figure 5:
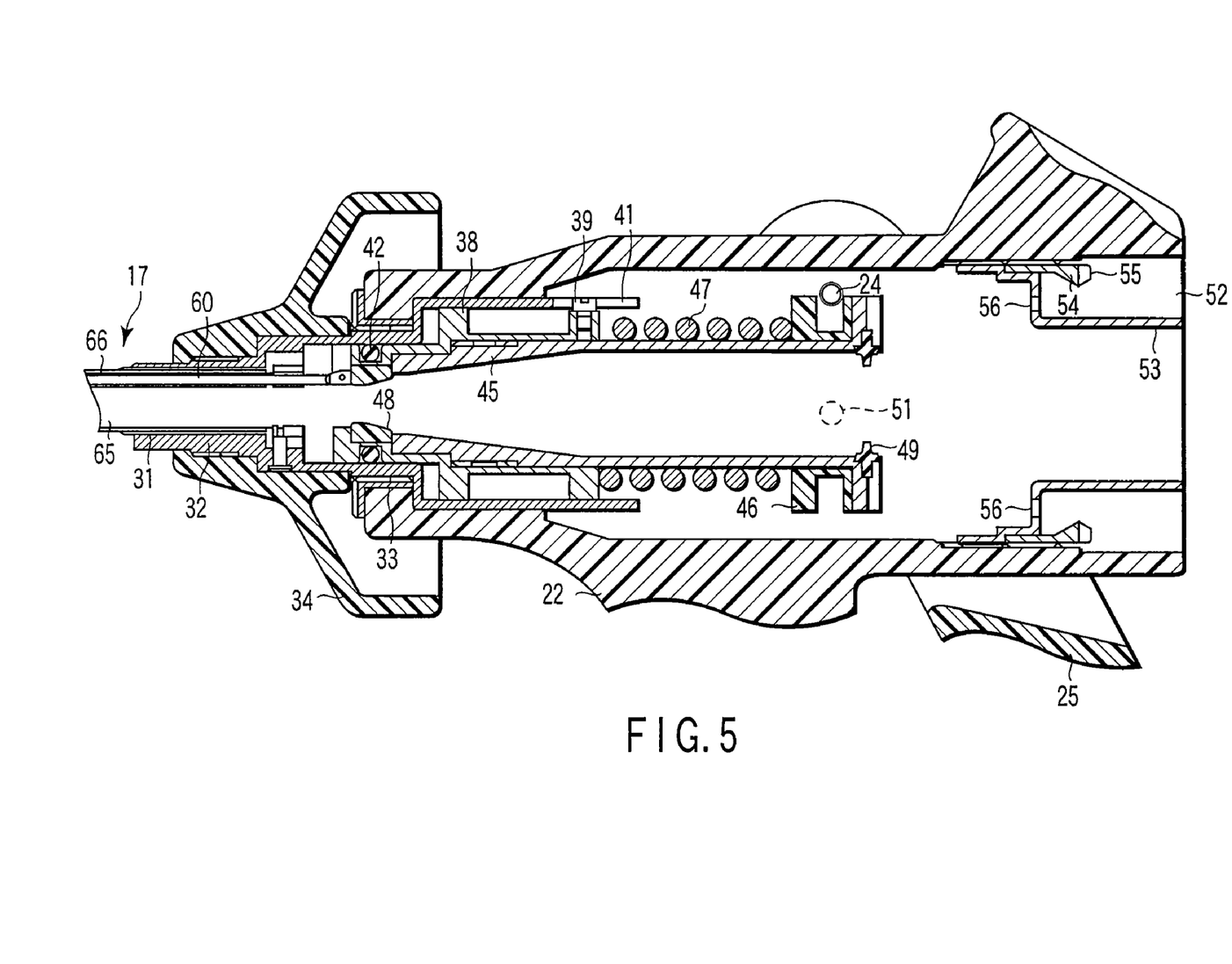
FIG. 5 is a vertical sectional view of an operation portion in the handle unit of the ultrasonic treatment instrument.

As shown in FIG. 5, a cylindrical joint member 32 disposed in the operation portion main body 22 via a pipe fixing member 31 is fixed/connected to the proximate-end portion of the insertion sheath portion 17. The joint member 32 is attached to the operation portion main body 22 by a fixing ring 33 so as to rotatable around an insertion portion axis. A rotary operation knob 34 is fixed to the joint member 32. When the rotary operation knob 34 is rotated/operated, the insertion sheath portion 17 can be rotated/operated around a sheath axis.

A cylindrical driving force transmission intermediate member 38 to be connected to an operation rod 60 described later is fitted in the joint member 32 so as to be movable in an insertion portion axial direction. A pin 39 is attached to a rear-end portion of the driving force transmission intermediate member 38. This pin 39 is fitted/engaged in a guide groove 41 which is cut/formed in the joint member 32 so as to extend in the insertion portion axial direction. This regulates the rotation of the driving force transmission intermediate member 38 and allows only the movement into the insertion portion axial direction. An O ring 42 is fitted around the outer periphery of the distal-end portion of the driving force transmission intermediate member 38, and the O ring 42 is disposed between the driving force transmission intermediate member 38 and joint member 32.

As shown in FIG. 5, a distal-end outer peripheral portion of a slider receiver member 45 is screwed in the driving force transmission intermediate member 38, and both the portion and the member are coaxially assembled/fixed. A slider member 46 is slidably fitted in the outer periphery of the driving force transmission intermediate member 38 on the side of the rear end. A coiled spring 47 is wound around the outer periphery of the slider receiver member 45 between the driving force transmission intermediate member 38 and the slider member 46.

A first packing 48 in the form of the O ring is attached to the inner surface of the driving force transmission intermediate member 38. When the probe unit 3 is attached to the handle unit 2, the first packing 48 is bonded to the outer periphery of the vibration transmission member 10 of the probe unit 3 to hold the vibration transmission member 10 and to close a gap between the units. A second packing 49 having the O-ring shape is attached to a hand-side end of the slider receiver member 45. When the probe unit 3 is attached to the handle unit 2, the second packing 49 is bonded to the outer periphery of the vibration transmission member 10 of the probe unit 3 to hold the vibration transmission member 10 and to close the gap between the units.

Since the packings 48, 49 are disposed in this manner, for example, aeroperitoneum gas at the time of a surgical operation under an abdominoscope can be prevented from passing through an inner gap from an insertion portion distal-end and leaking. Since two packings 48, 49 are both formed of a rubber, and elastic, the vibration transmission member 10 to ultrasonically vibrate is steadily supported without any difficulty.

An engaging pin 51 to engage with the slider member 46 in the operation portion main body 22 is disposed in the movable handle 25 of the handle unit 2. When the movable handle 25 is rotated centering on the handle support shaft 24, the movement of the movable handle 25 is transmitted to the slider member 46 via the engaging pin 51. Since the helical compression spring 47 is constantly attached in a compressed/urged state, a certain or more operation force applied to the movable handle 25 in a closing direction is absorbed by deformation of the helical compression spring 47. Accordingly, the slider receiver member 45 is slid/operated in a state in which an overload applied to the slider receiver member 45 is prevented.

As shown in FIG. 5, a vibrator connection portion 52 for detachably attaching the vibrator unit 4 is disposed in a rear-end portion in the operation portion main body 22 of the handle unit 2. The vibrator connection portion 52 includes a cylindrically formed frame member 53 and a cylindrical connection member 54. The frame member 53 and connection member 54 are screwed/fixed into the inner surface of the operation portion main body 22. A screwed/fixed portion of the frame member 53 is positioned before the connection member 54. The rear-end portion of the frame member 53 is concentrically disposed inside the connection member 54. When the vibrator unit 4 is attached to the handle unit 2, a front-end portion of the cylindrical exterior cover 5 of the vibrator unit 4 is fitted between the frame member 53 and connection member 54. The connection portion 9 of the vibrator unit 4 is fitted into/engaged with a distal-end engagement portion 55 of the frame member 53, so that the vibrator unit 4 is fixed to the handle unit 2. The connection portion 9 is formed, for example, by a C ring so as to swell outwards. A plurality of through-holes 56 are appropriately scattered and disposed in a wall portion of the frame member 53.

Figure 4A:
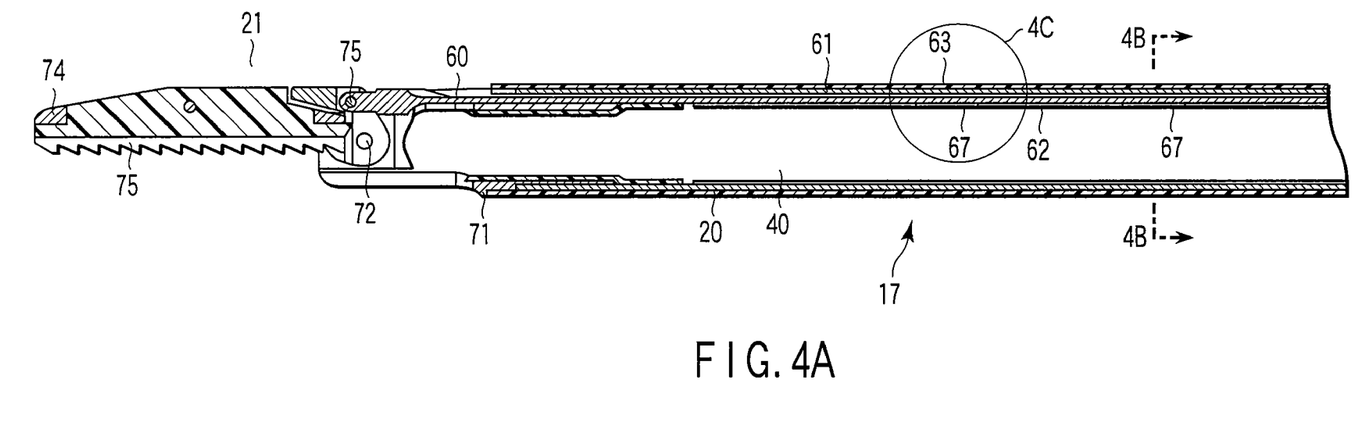
FIG. 4A is a vertical sectional view of an insertion sheath portion in the handle unit of the ultrasonic treatment instrument.
Figure 4B:
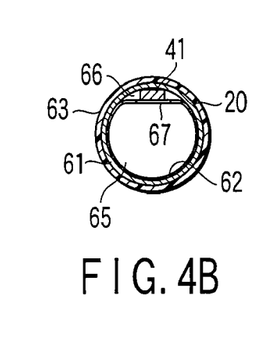
FIG. 4B is a transverse sectional view of the insertion sheath portion in the handle unit along a line 4B-4B in FIG. 4A.
Figure 4C:
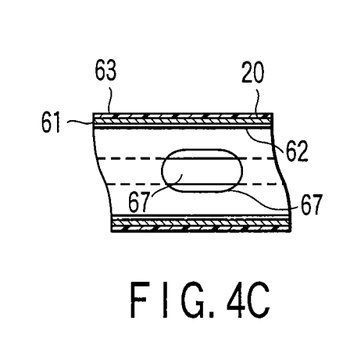
FIG. 4C is a vertical sectional view of the insertion sheath portion in the handle unit in the vicinity of part 4C in FIG. 4A.

Next, the insertion sheath portion 17 of the handle unit 2 will be described. As shown in FIG. 4A, the overcoat tube 20 of the insertion sheath portion 17 includes an outer pipe (overcoat tube) 61 and an inner pipe 62, and the outer periphery of the outer pipe 61 is subjected to an electric insulating treatment by an insulating tube 63. In the electric insulation, the insertion sheath portion 17 may also be subjected to treatment means such as coating. As shown in FIG. 4B, the outer pipe 61 includes a main channel 65 for passing the vibration transmission member 10 of the probe unit 3, and a sub-channel 66 for passing the operation rod 60. Similarly, as shown in FIG. 4B, for the inner pipe 62 forming the main channel 65, a part of a circular sectional portion is crushed to be flat to form a gap as the sub-channel 66 between the section and the inner surface of the outer pipe 61. A through-hole 67 is formed in one or more appropriate portions of the inner pipe 62 disposed opposite to the sub-channel 66, so that the main channel 65 can be connected to the sub-channel 66.

As shown in FIG. 4A, the distal-end function portion 21 of the handle unit 2 includes a distal-end chip member 71 attached to the distal-end portion of the outer pipe 61 and formed, for example, of a metal, and a single swing hold member 74 rotatably attached to the distal-end chip member 71 via a support shaft 72. This hold member 74 holds a grasp member 75. The distal-end of the operation rod 60 is connected to the proximate-end portion of the hold member 74 via a support shaft 76. When the movable handle 25 is rotated to move the operation rod 60 forwards/backwards, the hold member 74 rotates, and an operation of opening/closing the distal-end function portion 21 is carried out. When the distal-end function portion 21 is disposed opposite to the distal-end portion 15 of the probe unit 3 in the vibration transmission member 10, and a living tissue of a treatment object is grasped by both the portions, a vibration energy is transmitted to the living tissue from the vibration transmission member 10.

Figure 6:
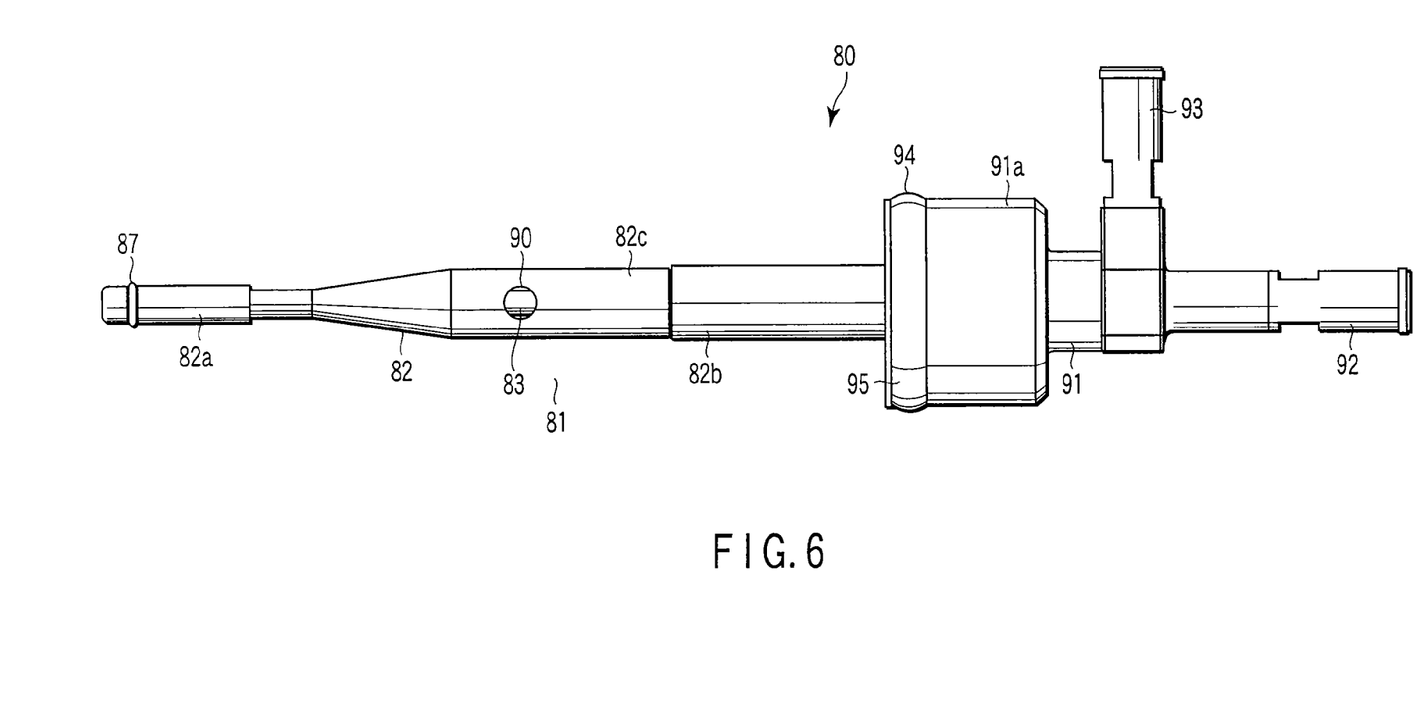
FIG. 6 is a side view of a cleaning device according to the first embodiment of the present invention.
Figures 7A, 7B:
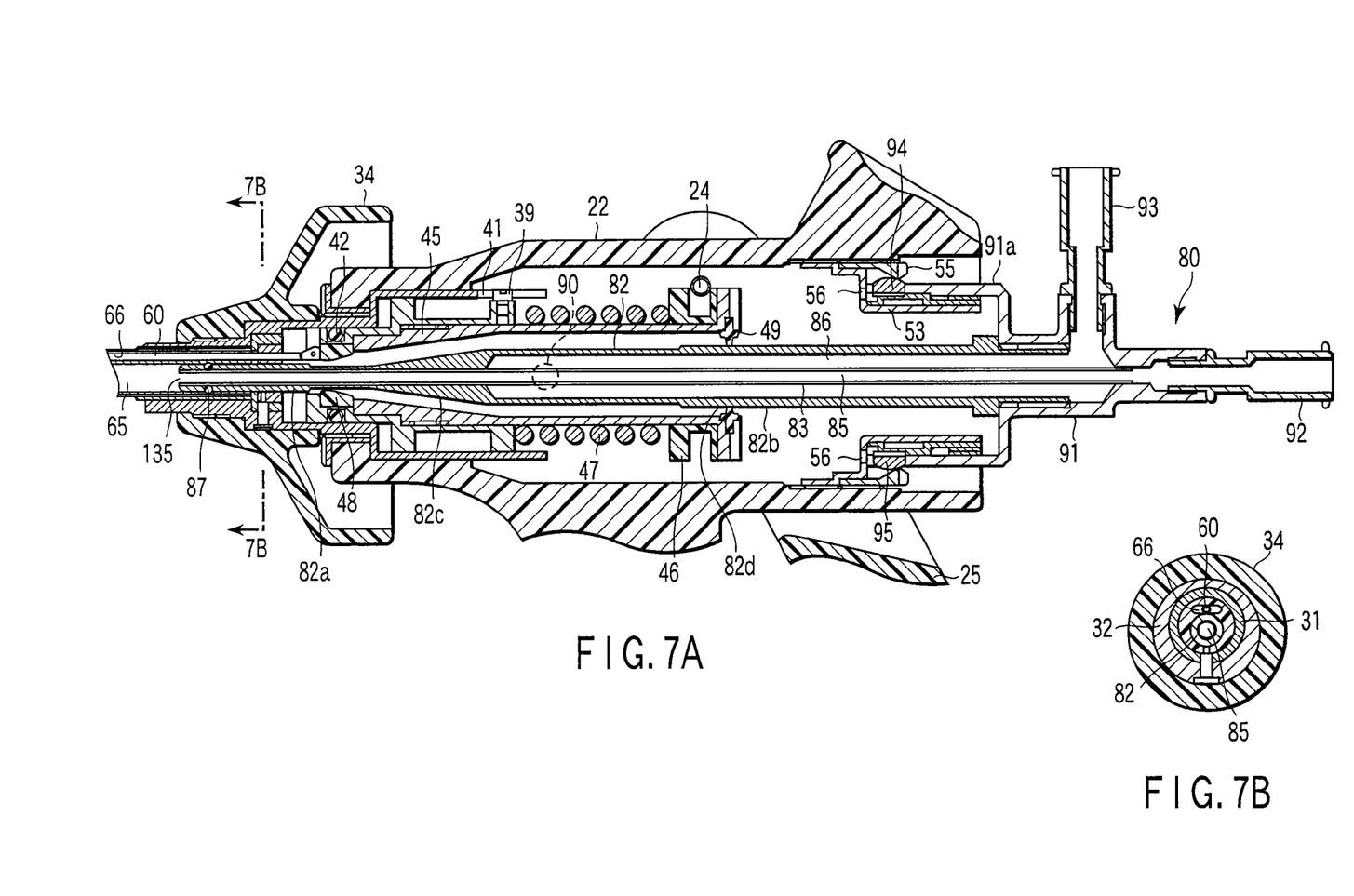
FIG. 7A is a vertical sectional view showing a state in which the cleaning device is attached to an operation portion of the ultrasonic treatment instrument.
FIG. 7B is a transverse sectional view of a part along line 7B-7B in FIG. 7A.

Next, a cleaning device 80 for cleaning the ultrasonic treatment instrument 1 will be described. As shown in FIG. 6, the cleaning device 80 includes a nozzle main body 81 detachably attached to the operation portion 19 of the handle unit 2. As shown in FIG. 7A, the nozzle main body 81 is inserted into the handle unit 2 from which the probe unit 3 of the ultrasonic treatment instrument 1 has been removed, and is accordingly attached to the handle unit 2, and the ultrasonic treatment instrument 1 is used in this state. The nozzle main body 81 is not limited to a metal material.

As shown in FIG. 7A, the nozzle main body 81 of the cleaning device 80 is constituted of a double pipe structure including an outer pipe 82 and inner pipe 83. To attach the nozzle main body 81 to the operation portion 19 of the handle unit 2 from which the probe unit 3 has been removed, the distal-end portion of the nozzle main body is inserted until reaching the main channel 65 of the insertion sheath portion 17. A packing for sealing 87 in the form of the O ring is attached to the outer periphery of a distal-end portion 82a of the outer pipe 82 of the nozzle main body 81. The packing 87 constitutes first seal means for sealing a gap in the main channel 65, when the distal-end portion 82a of the nozzle main body 81 is inserted in the main channel 65 of the handle unit 2. This packing 87 constitutes an engaging portion for attaching the distal-end portion 82a inserted in an inlet of the main channel 65 to the medical instrument 1.

A hand-side portion 82b of the outer pipe 82 positioned in the operation portion 19 of the handle unit 2 is formed to be thicker than the distal-end portion 82a. The outer periphery of the hand-side portion 82b having a large diameter constitutes second seal means for sealing a gap, when the nozzle main body 81 is inserted into the handle unit 2 to closely contact the second packing 49 in the handle unit 2 with pressure. The outer peripheral portion of the hand-side portion 82b having the large diameter constitutes an engaging portion 82d which engages with the second packing 49 of the medical instrument 1. As shown in FIG. 7, a portion in a region between the distal-end portion 82a and hand-side portion 82b of the outer pipe 82 of the nozzle main body 81 is formed as an intermediate portion 82c which is thicker than the distal-end portion 82a and is thinner than the hand-side portion 82b.

The inner pipe 83 is linearly disposed extending over the hand-side portion 82b from the distal-end portion 82a in the outer pipe 82 of the nozzle main body 81. Moreover, the inner pipe 83 forms a first water supply channel 85 leading to the main channel 65. The distal-end of the inner pipe 83 forms a first water supply nozzle port 135 leading to the main channel 65. An outside space of the inner pipe 83 in the hand-side portion 82b having the large diameter forms a second water supply channel 86 leading to the sub-channel 66. One or more water discharge ports (holes) 90 are formed in a portion positioned behind the packing 87 of the first seal means and positioned before the portion of the second packing 49 constituting the second seal means, that is, in a portion of the intermediate portion 82c herein. The water discharge port 90 forms a second water supply nozzle port for supplying water to the sub-channel 66 from the second water supply channel 86 of the nozzle main body 81 via a gap between the outside of the outer pipe 82 and the inside of the slider receiver member 45. The first water supply channel 85 leading to the main channel 65 and the second water supply channel 86 leading to the sub-channel 66 are formed independently of each other. The water supply ports are independently and individually connected to the main channel 65 and sub-channel 66.

As shown in FIG. 7A, a supply nozzle member 91 is attached to the proximate-end of the nozzle main body 81. The supply nozzle inlet member 91 includes a first supply inlet 92 leading to the first water supply channel 85, and a second supply inlet 93 leading to the second water supply channel 86. The first supply inlet 92 is coaxially disposed toward a rear part with respect to the axial direction of the nozzle main body 81. The second supply inlet 93 is disposed in an intermediate portion of the supply nozzle member 91 so as to protrude sideward with respect to the axial direction of the nozzle main body 81. Furthermore, a front-end frame portion 91a of the supply nozzle member 91 is extended in a thick cylindrical shape, and a connection portion 94 including a structure similar to that of the connection portion 9 of the probe unit 3 is constituted in the front-end frame portion. For example, a C ring 95 is attached to the connection portion 94 to form a shape swelling outwards. The connection portion 94 is fitted into and engaged with the distal-end engagement portion 55 of the frame member 53 of the handle unit 2 to attachably/detachably fix the nozzle main body 81 to the handle unit 2.

Next, a function in a case in which the cleaning device 80 of the present embodiment is used to clean the ultrasonic treatment instrument 1 will be described.

To use the ultrasonic treatment instrument 1, the handle unit 2, probe unit 3, and vibrator unit 4 are assembled in a state shown in FIG. 1. Moreover, when the ultrasonic treatment instrument 1 is used, the ultrasonic treatment instrument 1 becomes dirty. Therefore, the instrument needs to be cleaned every use.

Here, apparent dirt on the surface of the ultrasonic treatment instrument 1 can quickly be removed to a certain degree even by shower cleaning with a treatment instrument cleaner or by exposure to running water, but the inside of the main channel 65 passed through the vibration transmission member 10 of the probe unit 3 or the inside of the sub-channel 66 passed through the operation rod 60 for operating the distal-end function portion 21 also becomes dirty. The dirt inside the channel cannot quickly or easily be removed even by the shower cleaning or the exposure to the running water.

To solve the problem, the cleaning device 80 of the present embodiment is used to remove the dirt inside the main channel 65 or the sub-channel 66. That is, as shown in FIG. 7A, the nozzle main body 81 is inserted into the operation portion 19 of the handle unit 2 from which the probe unit 3 has been removed, and the connection portion 94 of the nozzle main body 81 is fitted into/engaged with the distal-end engagement portion 55 in the frame member 53 of the handle unit 2 to fix the nozzle main body 81 to the handle unit 2. At this time, the water supply port of the first water supply channel 85 leads only to the main channel 65, and the water supply port of the second water supply channel 86 leads only to the sub-channel 66.

Subsequently, supply tube line means such as a water supply tube connected to a water supply is individually connected to the first supply inlet 92 and second supply inlet 93 of the supply nozzle member 91. As the water supply, it is possible to use a water supply tank or pump in which the treatment instruments such as the ultrasonic treatment instrument are disposed and which is incorporated in the cleaner for the treatment instrument, to carry out the shower or running water cleaning. Two water supply tubes (not shown) connected to the water supply are separately connected to the first supply inlet 92 and second supply inlet 93.

Pressurized cleaning water from the water supply through the respective water supply tubes separately connected to the first supply inlet 92 and second supply inlet 93 is supplied to the main channel 65 via the first water supply channel 85, and also supplied to the sub-channel 66 via the second water supply channel 86. The high-pressure cleaning water pressurized from the water supply is forcibly supplied to the main channel 65 and sub-channel 66. Therefore, the dirt inside the main channel 65 and sub-channel 66 is passed together with the cleaning water on the distal-end side of each channel, so that the dirt inside the channels can strongly be removed. The pressurized cleaning water from the water supply is independently and separately supplied to the main channel 65 and sub-channel 66. This can prevent the cleaning water from running only in one direction by a difference in channel resistance between the channels. Especially, the supply of the cleaning water into the thin sub-channel 66 can be prevented from weakening, and both the channels 65, 66 can securely be cleaned without any unevenness.

In the cleaning treatment, the ultrasonic treatment instrument 1 to which the cleaning device 80 has been attached is installed in a cleaning tank or tray in the cleaner, and the apparent surface part of the ultrasonic treatment instrument 1 is preferably simultaneously cleaned by the shower cleaning or by the exposure into the running water.

The cleaning device according to a second embodiment of the present invention will be described with reference to FIGS. 8A and 8B. In the present embodiment, the same components as those of the first embodiment are denoted with the same reference numerals, and detailed description thereof is omitted.

Figures 8A, 8B:
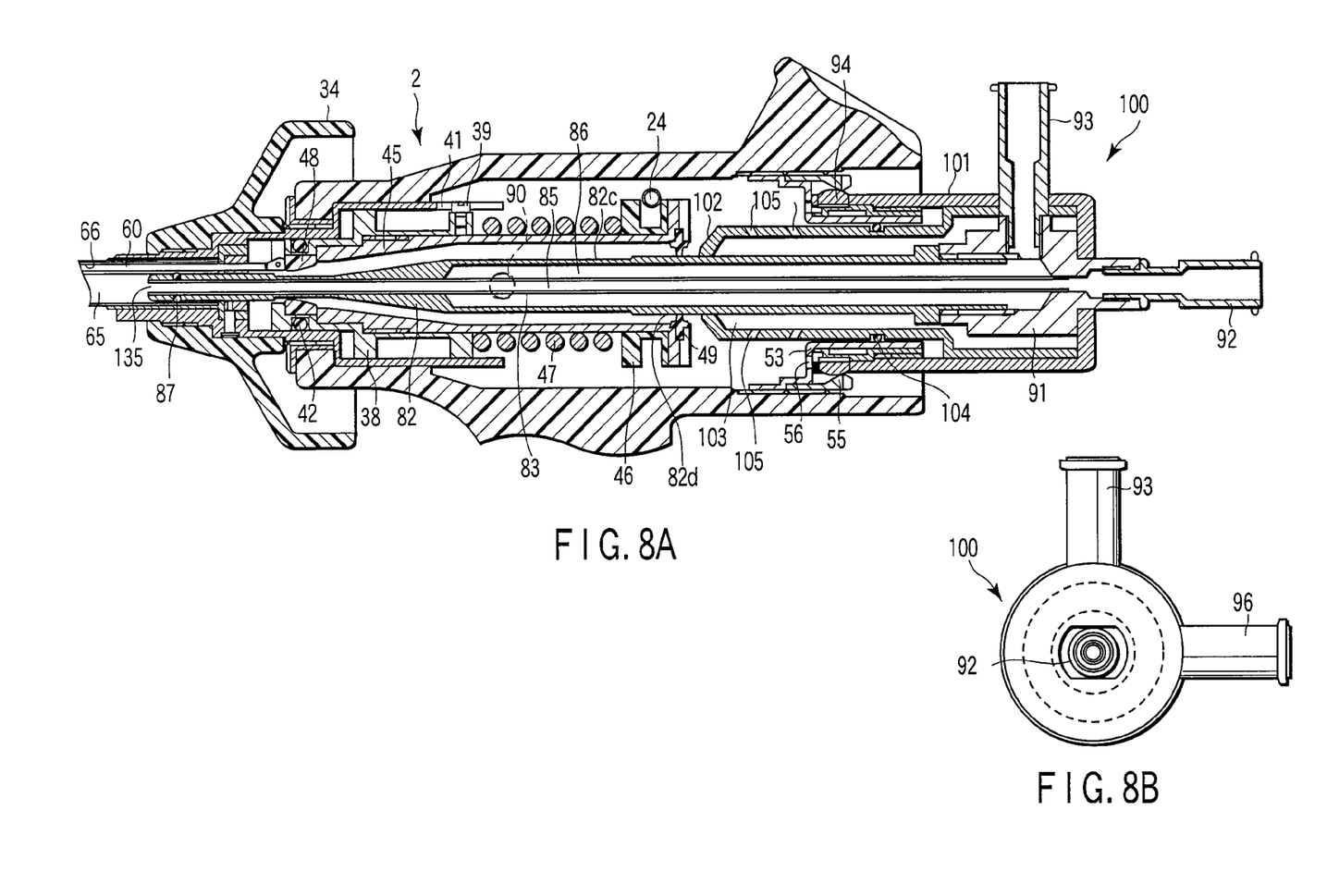
FIG. 8A is a vertical sectional view in a state in which cleaning device according to a second embodiment of the present invention is attached to the operation portion of the ultrasonic treatment instrument.
FIG. 8B is a rear view of the cleaning device seen on hand.

As shown in FIGS. 8A and 8B, in a cleaning device 100 according to the present embodiment, a frame member 101 and a cylindrical water supply port member 102 which are separate members are added to the supply nozzle member 91. As shown in FIG. 8A, in the same manner as in the first embodiment, the frame member 101 includes the connection portion 94 which is fitted into the distal-end engagement portion 55 of the frame member 53 of the handle unit 2 and engaged with the distal-end engagement portion 55. The cylindrical water supply port member 102 is coaxially disposed in the frame member 101, and the distal-end portion extends ahead of the frame member 101 to surround the outer periphery of the outer pipe 82. A space between the outer pipe 82 and the water supply port member 102 forms a third water supply channel 103. A third supply inlet 96 is disposed in rear-end portions of the frame member 101 and water supply port member 102. The third supply inlet 96 is connected to the third water supply channel 103.

As shown in FIG. 8A, the water supply port member 102 is substantially closely fitted into the inner surface of the frame member 53 of the handle unit 2, and is positioned in this state. A packing 104 constituting third seal means is disposed in the outer periphery of the water supply port member 102. When the supply nozzle member 91 is attached to the handle unit 2, the packing 104 seals between the frame member 53 and water supply port member 102 of the handle unit 2. One or more water supply ports (holes) 105 connected to the third water supply channel 103 are positioned before a position where the packing 104 is disposed, and disposed in an outer peripheral wall of the water supply port member 102.

When the cleaning device 100 according to the present embodiment is used, in the same manner as in the first embodiment, the nozzle main body 81 is inserted in the operation portion 19 of the handle unit 2 from which the probe unit 3 has been removed. The connection portion 94 of the nozzle main body 81 is fitted into/engaged with the distal-end engagement portion 55 in the frame member 53 of the handle unit 2 to fix the nozzle main body 81 to the handle unit 2. At this time, the water supply port of the first water supply channel 85 is connected to the main channel 65, and the water supply port of the second water supply channel 86 is connected to the sub-channel 66. Simultaneously, one or more water supply ports 105 connected to the third water supply channel 103 are directly connected to an inner space of the operation portion 19 of the handle unit 2.

Supply pipe line means such as a water supply tube connected to the water supply is individually connected to the first supply inlet 92, second supply inlet 93, and third supply inlet 96. In the same manner as in the first embodiment, as the water supply, it is possible to use a water supply pump incorporated in a treatment instrument cleaning machine in which the treatment instruments such as the ultrasonic treatment instrument are disposed to carry out the shower cleaning or the running water cleaning.

The pressurized cleaning water from the water supply is supplied to the main channel 65 via the first water supply channel 85 through each water supply tube separately connected to the first supply inlet 92 and second supply inlet 93, and is supplied to the sub channel 66 via the second water supply channel 86. The pressurized cleaning water from the water supply is forcibly supplied to the main channel 65 and sub-channel 66. Therefore, the dirt in the main channel 65 and sub-channel 66 is passed together with the cleaning water on the side of the distal-end of each channel, and the dirt in the channel can strongly be removed.

Additionally, the pressurized cleaning water from the water supply is spouted into the inner space of the operation portion 19 of the handle unit 2 from one or more water supply ports 105 via the third water supply channel 103 through the water supply tube connected to the third supply inlet 96, and the inside of the operation portion 19 of the handle unit 2 is cleaned with the cleaning water. The cleaning water which has overflowed in the inner space of the operation portion 19 flows out to the outside of the operation portion 19 through the through-holes 56 of the frame member 53. Therefore, a peripheral region of the frame member 53 can be cleaned by the cleaning water flowing outwards from the inside. The cleaning water which has overflowed in the inner space of the operation portion 19 can be discharged to the outside through window holes (not shown) formed in a side wall of the operation portion 19 of the handle unit 2, because the engaging pin 51 of the movable handle 25 can movably be passed, and the inside of the operation portion 19 can be cleaned with the cleaning water flowing outwards from the inside.

A third embodiment of the present invention will be described with reference to FIG. 9. In the present embodiment, the same components as those of the first embodiment are denoted with the same reference numerals, and the detailed description is omitted.

The present embodiment is different from the ultrasonic treatment instrument of the first embodiment in that the ultrasonic treatment instrument which is the surgical treatment instrument as the cleaning object uses the probe unit 3 to supply a high-frequency current to the treatment portion.

Figure 9:
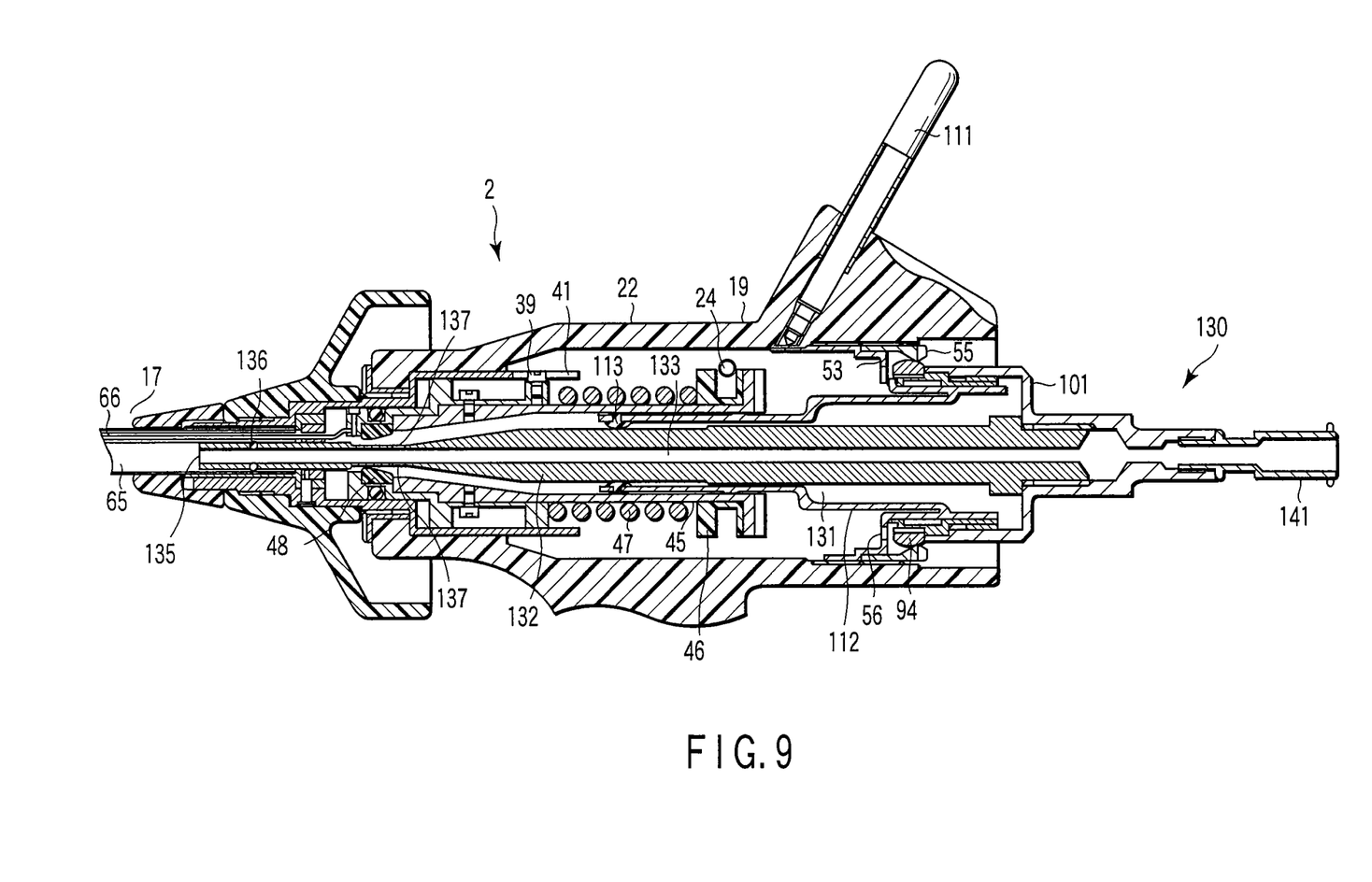
FIG. 9 is a vertical sectional view in a state in which the cleaning device according to a third embodiment of the present invention is attached to the operation portion of another type of the ultrasonic treatment instrument.

That is, for the ultrasonic treatment instrument of the present embodiment, as shown in FIG. 9, a high-frequency connection pin 111 is disposed in the electrically insulating operation portion main body 22 in the handle unit 2. The high-frequency connection pin 111 is connected to a power supply cord (not shown), and receives supply of a high-frequency current from an external high-frequency power supply. A cylindrical contact-point member 112 is disposed in the operation portion 19 in the handle unit 2. A rear end of the contact-point member 112 is fitted in the frame member 53 formed in a cylindrical shape. The contact-point member 112 is connected to the high-frequency connection pin 111 via the conductive frame member 53.

A front-end portion of the contact-point member 112 is slidably inserted in the cylindrical slider receiver member 45. An annular packing 113 is attached to the distal-end of the contact-point member 112, and also serves as an electric contact in contact with the outer periphery of the vibration transmission member 10 of the probe unit 3 attached to the handle unit 2. The packing 113 is connected to the high-frequency connection pin 111 via the contact-point member 112 and frame member 53. The packing 113 constitutes seal means in contact with the outer periphery of the nozzle main body of a cleaning device 130, when the cleaning device 130 of the present embodiment is mounted.

The cleaning device 130 of the present embodiment includes a water supply nozzle member 132 formed by one pipe material 131, and the pipe material 131 is constituted in the same manner as in the outer pipe 82 of the first embodiment. The water supply nozzle member 132 includes a mode of a single pipe in which the inner pipe 83 in the first embodiment is not disposed. For the pipe material 131, an inner hole forms one water supply channel 133. The distal-end of the pipe material 131 forms a water supply port 135 leading to the main channel 65 of the handle unit 2, when the cleaning device 130 is attached to the handle unit 2.

A packing for sealing 136 in the form of the O ring is attached to the outer periphery of the distal-end portion in the pipe material 131 of the water supply nozzle member 132. The packing 136 constitutes the seal means for blocking connection to the main channel 65 of the handle unit 2.

By the packing 136, one or more discharge paths (holes) 137 for connecting the water supply channel 133 to the outside can also be formed in the distal-end portion of the pipe material 131 of the water supply nozzle member 132 in a region extending to the seal means which contacts the packing 113. The discharge paths 137 lead to the sub-channel 66 of the handle unit 2, when the cleaning device 130 is attached to the handle unit 2. A water supply nozzle 141 connected to the water supply channel 133 is disposed in the rear end of the pipe material 131 of the water supply nozzle member 132.

Then, when the cleaning device 130 of the present embodiment is used, the device is attached to the ultrasonic treatment instrument in the same manner as in the first embodiment. The cleaning water from a supply tube (not shown) connected to the water supply inlet 141 is supplied to the main channel 65 of the handle unit 2 from the water supply port 135 through only one water supply channel 133 of the water supply nozzle member 132.

On the other hand, when one or more discharge paths 137 are disposed, a part of the cleaning water supplied to the water supply channel 133 is discharged to the outside of the water supply nozzle member 132 midway from the water supply channel 133 through one or more discharge paths 137, and is also supplied to the sub-channel 66. The main channel 65 and sub-channel 66 can simultaneously be cleaned.

Even when one or more discharge paths 137 are not disposed, the main channel 65 is connected to the sub-channel 66 via the through-hole 67 formed in the inner pipe 62 in the overcoat tube 20 of the insertion sheath portion 17 of the ultrasonic treatment instrument (see FIG. 4A). Then, the main channel 65 is connected to the sub-channel 66, the cleaning water mutually flows, and this promotes the cleaning of the main channel 65 and sub-channel 66.

The same device as the cleaning device 80 according to the first embodiment can be used as the device for cleaning an ultrasonic treatment instrument 110.

As described above, according to the cleaning device of the present invention, especially the channel of the medical instrument, which is not easily cleaned, can efficiently be cleaned.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. A cleaning device using cleaning water to clean both channels of a medical instrument including a first channel and second channel and a portion via which both the channels are connected to each other, comprising:

a tubular member including a proximate-end portion and a distal-end portion which able to be inserted in an inlet of the first channel of the medical instrument;

a first water supply port which is disposed in the distal-end portion and which leads to the first channel to supply the cleaning water to the first channel, when the distal-end portion is inserted in the inlet;

a first seal member which is disposed on an outer peripheral surface of the distal-end portion and which is positioned and disposed on a proximate-end side from the water supply port to seal a gap between an outer peripheral portion of the distal-end portion and an inner surface of the first channel and to constitute a first engaging portion which attaches the distal-end portion inserted in the inlet to the medical instrument, when the distal-end portion is inserted in the inlet;

a second water supply port which is disposed in the tubular member and which is positioned and disposed in a proximate-end side portion partitioned from the first water supply port by the first seal member when the distal-end portion is inserted in the inlet and which leads to the second channel to supply the cleaning water to the second channel;

a second engaging portion which is disposed in the tubular member and which is positioned and disposed on the proximate-end side from the second water supply port and which is constituted by an outer peripheral portion sealing from a seal member of the medical instrument, when the distal-end portion is inserted in the inlet;

a first inlet port which is disposed in the proximate-end portion of the tubular member and which is connected to the first water supply port and which is to be connected to a water supply source of the cleaning water; and a second inlet port which is disposed in the proximate-end portion of the tubular member and which is connected to the second water supply port and which is to be connected to the water supply source of the cleaning water.

2. The cleaning device according to claim 1, further comprising:

an engagement portion which is detachably attached to an attachment portion of the medical instrument, to attach a unit to the medical instrument, and which fixes the tubular member to the medical instrument.

3. The cleaning device according to claim 1, further comprising:

a third water supply port which is positioned on the proximate-end side from the second engaging portion and which is disposed in the tubular member and which supplies the cleaning water into the medical instrument; and a third port which is disposed in the tubular member and which leads to the third water supply port and which is connected to the water supply source of the cleaning water.

4. A cleaning device using cleaning water to clean channels of a medical instrument which includes a first channel which passes a treatment probe to transmit a treatment energy, a grasp member for grasping a living tissue with a distal-end portion of the treatment probe, a rod for operating the grasp member, and a second channel for passing the rod and to which a generation unit for generating the treatment energy is detachably attached, the device comprising:

an elongated member including a proximate-end portion and a distal-end portion which able to be inserted in an inlet of the first channel;

an attachment member which is disposed in the proximate-end portion and which able to be attached to the medical instrument;

a first water supply port which is disposed in the distal-end portion and which supplies the cleaning water to the first channel;

a first engaging portion which includes a member disposed on an outer peripheral surface of the distal-end portion to seal a gap between the outer peripheral surface and an inner surface of the inlet and which is constituted of the member to attach the distal-end portion inserted in the inlet to the inner surface of the inlet;

a second engaging portion which is positioned and disposed on the proximate-end side from a portion for connecting the first channel to the second channel in the elongated member and which includes a large-diameter portion formed to be thicker than the distal-end portion and which engages with the medical instrument by the large-diameter portion;

a second water supply port which is positioned between the first engaging portion and the second engaging portion to open in an outer peripheral wall of the elongated member and which leads to the second channel and which supplies water to the second channel;

a first supply inlet port which is disposed in the elongated member and which is connected to the first water supply port and which is to be connected to a water supply of the cleaning water to supply the water to the first water supply port; and a second supply inlet port which is disposed in the elongated member and which is connected to the second water supply port and which is to be connected to the water supply source of the cleaning water to supply the water to the second water supply port.

5. The cleaning device according to claim 4, further comprising:

an engagement portion which is detachably attached and fixed to an attachment portion of the medical instrument, to attach a unit to the medical instrument.

6. The cleaning device according to claim 4, further comprising:

a third water supply port which is positioned on the proximate-end side from the second engaging portion and which is disposed in the tubular member and which supplies the cleaning water into the medical instrument; and a third port which is disposed in the tubular member and which leads to the third water supply port and which is connected to the water supply source of the cleaning water.

* * * * *